US008658184B2

(12) United States Patent  
Schulz et al.

(10) Patent No.: US 8,658,184 B2  
(45) Date of Patent: Feb. 25, 2014

(54) GLASS FLAKES, AND THE USE THEREOF AS TRANSPARENT FILLER

(75) Inventors: Elke Schulz, Erzhausen (DE); Veronika Hochstein, Bruchsal (DE)

(73) Assignee: Merck Patent GmbH, Darmstadt (DE)

( * ) Notice: Subject to any disclaimer, the term of this patent is extended or adjusted under 35 U.S.C. 154(b) by 635 days.

(21) Appl. No.: 11/727,095

(22) Filed: Mar. 23, 2007

(65) Prior Publication Data

US 2007/0225424 A1    Sep. 27, 2007

(30) Foreign Application Priority Data

Mar. 24, 2006 (DE) .......................... 10 2006 014 095

(51) Int. Cl.
 B32B 33/00     (2006.01)
 C08K 3/40      (2006.01)
 B32B 5/16      (2006.01)
 B32B 17/06     (2006.01)

(52) U.S. Cl.
 USPC .......................... 424/401; 524/494; 428/404

(58) Field of Classification Search
 USPC ....................................................... 424/401
 See application file for complete search history.

(56) References Cited

U.S. PATENT DOCUMENTS

| | | | |
|---|---|---|---|
| 3,087,828 A | | 4/1963 | Linton et al. |
| 3,138,475 A | | 6/1964 | Schroder et al. |
| 3,331,699 A | | 7/1967 | Marshall et al. |
| 3,969,128 A | * | 7/1976 | Urs ............. 106/287.1 |
| 4,867,793 A | | 9/1989 | Franz |
| 5,221,341 A | | 6/1993 | Franz et al. |
| 5,290,544 A | * | 3/1994 | Shimono et al. ......... 424/63 |
| 5,433,779 A | | 7/1995 | Deluca, Jr. |
| 5,436,077 A | | 7/1995 | Matsuba et al. |
| 5,540,769 A | | 7/1996 | Franz |
| 5,753,371 A | * | 5/1998 | Sullivan et al. ........... 428/406 |
| 6,045,914 A | | 4/2000 | Sullivan et al. |
| 6,123,951 A | * | 9/2000 | Gueret et al. ............ 424/401 |
| 6,132,873 A | | 10/2000 | Dietz et al. |
| 6,238,471 B1 | | 5/2001 | Vogt et al. |
| 6,284,032 B2 | | 9/2001 | Andes et al. |
| 6,517,628 B1 | | 2/2003 | Pfaff et al. |
| 6,596,070 B1 | | 7/2003 | Schmidt et al. |
| 6,599,355 B1 | | 7/2003 | Schmidt et al. |
| 6,689,205 B1 | | 2/2004 | Bruckner et al. |
| 6,767,633 B2 | | 7/2004 | Steudel et al. |
| 6,777,085 B1 | * | 8/2004 | Argoitia et al. ............ 428/403 |
| 7,226,503 B2 | | 6/2007 | Anselmann et al. |
| 2003/0019501 A1 | * | 1/2003 | Hirota et al. ........... 132/73 |
| 2003/0176560 A1 | * | 9/2003 | Mueller et al. ........... 524/494 |
| 2004/0120908 A1 | * | 6/2004 | Cohen et al. ............ 424/63 |
| 2004/0170838 A1 | * | 9/2004 | Ambrosius et al. ........ 428/406 |
| 2005/0049133 A1 | * | 3/2005 | Fujiwara et al. ......... 501/70 |
| 2005/0113485 A1 | * | 5/2005 | Yokoi .................... 523/160 |
| 2007/0012487 A1 | | 1/2007 | Becker et al. |
| 2008/0190141 A1 | | 8/2008 | Watkinson |

FOREIGN PATENT DOCUMENTS

| | | |
|---|---|---|
| DE | 19951871 A1 | 5/2001 |
| DE | 10018904 | 10/2001 |
| EP | 0 289 240 | 11/1988 |
| EP | 0 671 161 | 9/1995 |
| EP | 1045014 | 10/2000 |
| JP | 200131421 A2 | 5/1990 |
| JP | 6116507 A2 | 4/1994 |
| JP | 6116508 A2 | 4/1994 |
| JP | 6116510 A2 | 4/1994 |
| JP | 7246366 | 9/1995 |
| JP | 9110452 A2 | 4/1997 |
| JP | 10279828 A | 10/1998 |
| JP | 2001-31421 | 2/2001 |
| WO | WO 9746624 | 12/1997 |
| WO | WO 9920695 | 4/1999 |
| WO | WO-2005 063637 | 7/2005 |

OTHER PUBLICATIONS

English translation of JP 7246366, "A pearlescent material and a paint that contains same", Inventor: Kiwa Yamane.
New glass flake pigment "Metashine" "Crystal Star" Toyo Aluminium K.K. Powder Paste Division, published Jul. 3, 1998.
G. Pfaff et al, "Angle-dependent optical effects deriving from submicron structures of films and pigments", Chemical Reviews, vol. 99, No. 7, pp. 1963-1981(199).
YTH Translation JP (A) H6-116508—translation of JP (A) H6-116508, Applied: Oct. 6, 1992—Application No. H4-267113, Laid-Open Date: Apr. 26, 1994—"Manufacturing Method of Flaky Substance Coated with Titania or Zirconia", Kazuhiro Doushita et al.
Patent Abstracts of Japan vol. 1999, No. 1, Jan. 29, 1999.
Patent Abstracts of Japan, "Production of flaky material coated with titania or zirconia", Apr. 26, 1994, (Chem. Abs. 121 (18) 207716A); JP6116508A2.
Patent Abstracts of Japan, vol. 1999, No. 1, Jan. 29, 1999 & JP 10279828 A (Merckx Japan), Oct. 20, 1998.
Shelby, J.E., "Introduction to glass sciences and technology", 1997, The royal society of chemistry, pp. 220-221.
Ketex, K.E. Textile Pvt. Ltd., webpages, 2002, KE technical textile private limited , pp. 1-5.
Saint-Gobain Vetrotex, Glass strand webpages, 2001, Saint-Gobain Vetrotex International, pp. 1-4.
Hartman et al, High strength glass fibers, written in 1996, publication No. LIT-2006-111, 2006, AGY, pp. 1-12.
Engeneering Handbook: Glass compositions. www.crystan.co.uk/products.
Wikipedia.org: Quarzglas—5 pages, no date.
YTH Translation—Glass Engineering Handbook, pp. 356 + 514, 7 pages, no date.

(Continued)

Primary Examiner — Janet Epps-Smith  
Assistant Examiner — Audrea Buckley  
(74) Attorney, Agent, or Firm — Millen, White, Zelano & Branigan, P.C.

(57) ABSTRACT

The present invention relates to glass flakes and to the use thereof, in particular as transparent filler in cosmetic formulations. Glass flakes having certain dimensions are suitable, owing to their transparency, as filler in cosmetic formulations since they do not change the basic color of the formulation and at the same time improve the skin feel.

20 Claims, No Drawings

(56) References Cited

OTHER PUBLICATIONS

Patent Abstracts of Japan, Publication No. 2001-031421, Publication Date: Feb. 6, 2001, 1 page.

English language translation of paragraph [0043] (p. 6, right column, line 19 to line 29) of JP 2001-31421, 1 page.

Spec Sheets for ECR Glassflake of Glassflake, Ltd., Apr. 2008, 4 pages.

Becker, M., Cosmetic spray technology marketing, COSSMA, Nov. 2009.

Buxbaum and Pfaff, Industrial Inorganic Pigments, Third, Completely Revised and Extended Edition, Wiley-VCH, May 9, 2005, pp. 4 and 44.

Marbert GMBH, "Ectoine and ectoine derivatives as moisturizing agents in cosmetic preparation," Data Supplied from espacenet database—Worldwide, Publication Date: Sep. 13, 1995; English Abstract of EP 0 671 161.

Nippon Sheet Glass Co Ltd., "Device for Manufacturing flake-shaped glass," Patent Abstracts of Japan, Publication Date: Aug. 14, 2001; English Abstract of JP-2001 220163.

Translation of Japanese Patent Specification No. JP 06-116507, Publication Date: Apr. 26, 1994.

Translation of Japanese Patent Specification No. JP-06-116510, Publication Date: Apr. 26, 1994.

Wikipedia definition of Sol-gel dated May 4, 2011 http://en.wikipedia.org/wiki/Sol-gel.

* cited by examiner

GLASS FLAKES, AND THE USE THEREOF AS TRANSPARENT FILLER

The present invention relates to glass flakes and to the use thereof, in particular as transparent filler in cosmetic formulations. Glass flakes having certain dimensions are suitable, owing to their transparency, as filler in cosmetic formulations since they do not change the basic color of the formulation and at the same time improve the skin feel. By contrast, colored glass flakes have the aim of changing the basic color of the formulation.

Cosmetic formulations, such as, for example, powders and make-ups, generally comprise organic and/or inorganic fillers. The fillers are particulate substances which do not cause any color effect in the product, i.e. in the cosmetic and dermatological composition itself or on the skin. For example, fillers from the group polymethyl methacrylate, methyl methacrylate crosspolymer, mica, nylon powder, pure or filled melamine resins, talc, $SiO_2$, kaolin, oxides or hydroxides of aluminium, magnesium, calcium, zinc, BiOCl, barium sulfate, calcium sulfate, calcium carbonate, basic alkaline-earth metal carbonates, such as, for example, calcium carbonate or magnesium carbonate, and carbon, and physical or chemical combinations of these substances, are employed in cosmetics. There are no restrictions regarding the particle shape of the filler. In accordance with requirements, it can be irregular, flake-form, spherical or needle-shaped. The commercially available fillers frequently exhibit the disadvantage of having an inherent color, which is generally undesired.

The invention is based on the object of finding fillers, in particular for cosmetic formulations, which enable the preparation of formulations which do not impair or specifically modify the basic color.

Surprisingly, it has now been found that amorphous glass flakes, which are preferred according to the invention, having precisely defined dimensions achieve this object.

The invention relates to transparent glass flakes which are distinguished by the fact that they have a thickness of <1 μm and an average particle size of 1-150 μm.

The glass flakes according to the invention are used, in particular, as filler in decorative and care cosmetics. However, they can also be employed in all formulations where fillers are usually employed, such as, for example, in inks, coatings and plastics.

In contrast to the prior art, where cosmetic formulations comprising glass powders having irregularly shaped particles are described, the glass flakes according to the invention exhibit a better filler behaviour and a very good skin feel.

Glass here is taken to mean an inorganic substance mixture which has cooled from the molten state without crystallisation and has taken on a solidified state. The glass flakes according to the invention are preferably amorphous.

Suitable glasses are all glasses known to the person skilled in the art, for example silicate glasses, such as soda-lime glass, borosilicate glass, aluminosilicate glass, lead crystal glass, E, A, C or ECR glass, Duran glass, window glass, laboratory glass, etc. Glasses of this type are produced from sand, lime, clay, boron compounds, potash, soda, etc. and allowed to solidify in a shaped state. Glass flakes according to the invention preferably consist of C, E, ECR or borosilicate glass. It is of course also possible to employ mixtures of different glass flakes which only differ in the glass composition.

The glass flakes can be specifically colored during production by addition of inorganic colorants. Suitable colorants are those which do not decompose at the melting point of the glass. The colorant is generally added to the glass melt in amounts of 0.1-50% by weight, in particular 0.2-25% by weight and very particularly preferably 0.5-10% by weight.

Suitable colorants are, in particular, the cations or complex anions of the elements Cu, Cr, Mn, Fe and Co and/or combinations thereof. Intense blue, green, yellow, orange or red colors can be obtained by addition of the ions. Suitable colorants are furthermore $TiO_2$ or elemental noble metals.

The glass flakes have a thickness of <1 μm, preferably 100 nm-1 μm, in particular 150-800 nm and very particularly preferably 200-600 nm. The average particle size is <150 μm, preferably 1-150 μm, in particular 10-100 μm and very particularly preferably 5-35 μm.

The glass flakes according to the invention preferably have an aspect ratio (diameter/thickness ratio) of 1-1500, in particular 10-700 and very particularly preferably 50-200.

The glass flakes are furthermore preferably distinguished by a refractive index of 1.2-2.1, in particular 1.3-1.9 and very particularly preferably 1.4-1.6.

The glass flakes are amorphous and preferably have a transparency of ≥90%, in particular ≥93%, and very particularly preferably ≥95% (measurement of the transmission in the spectral range from 400-700 nm using a UV/VIS/IR spectrometer: model Perkin Elmer Lambda 900 with Ulbricht sphere (diameter 150 mm)).

The glass flakes preferably have an oil absorption value (determined in accordance with DIN EN ISO 787-5: 1995-10) in the range from 20 to 130, in particular from 30 to 110, very particularly preferably from 50 to 90.

The glass flakes according to the invention are produced from the melt using known processes, such as, for example, tube blowing (Nippon Sheet Glass), spinning processes (Glassflake Ltd.). The glass flakes are particularly preferably produced by the spinning process, as described, for example, in EP 0 289 240 or WO 2005/063637.

In particular, the invention relates to optically clear uncolored and mass-colored glass flakes having thicknesses of <1 μm and an average particle size of 1-150 μm.

The glass flakes according to the invention are employed, in particular, as fillers, preferably in care and decorative cosmetics, since the transparent glass flakes are invisible in the formulation and thus do not distort the inherent color of the formulation.

Owing to the variable thicknesses and particle sizes, glitter effects which are readily visible under direct incidence of light can be produced specifically in the cosmetic formulations. With the aid of very thin glass flakes, preferably having thicknesses of <500 nm and/or very fine fractions having particle sizes of <50 μm, however, it is also possible to produce a matting effect, which is required, for example in face powders, for suppressing undesired sheen. A further effect is that skin sheen is reduced. The glass flakes according to the invention are furthermore distinguished by their very good skin feel. The use of the flakes according to the invention furthermore results in an improvement in the applicational properties of the formulation and the texture of the product, and purer colors of the formulation are obtained compared with the commercially available fillers.

The concentration of the glass flakes according to the invention in the application system to be pigmented is generally between 0.01 and 95% by weight, preferably between 0.1 and 50% by weight and in particular between 1.0 and 10% by weight, based on the total solids content of the system. It is generally dependent on the specific application and can be up to 95% by weight in the case of loose powders.

Preferably,
emulsions comprise 0.1-30% by weight, in particular 1-15% by weight, pigment-containing emulsions comprise 0.1-50% by weight, in particular 1-15% by weight, depending on the texture, toothpastes comprise 0.1-60% by weight, in particular 1-50% by weight, water-free oil/wax-based products comprise 0.1-75% by weight, in particular 0.5-65% by weight, powder products comprise 0.1-95% by weight, in particular 1-75% by weight, of glass flakes according to the invention, based on the formulation as a whole.

The glass flakes according to the invention are simple and easy to handle since they can be incorporated into a formulation very easily. The glass flakes can be incorporated into the application system alone or in the form of a mixture with further cosmetic assistants, carriers and active compounds by simple stirring-in. Complex dispersal of the glass flakes is unnecessary.

The glass flakes according to the invention can of course also be combined in the formulations with any type of cosmetic raw materials and assistants and active compounds. These include, inter alia, water, alcohols, polyols, polar and nonpolar oils, fats, waxes, film formers, polymers, copolymers, surfactants, free-radical scavengers, antioxidants, such as, for example, vitamin C or vitamin E, stabilisers, odour enhancers, silicone oils, emulsifiers, fragrances, solvents, such as, for example, ethanol, ethyl acetate or butyl acetate, preservatives and assistants which generally determine the applicational properties, such as, for example, thickeners and rheological additives, such as, for example, bentonites, hectorites, silicon dioxides, Ca silicates, gelatine, high-molecular-weight carbohydrates and/or surface-active assistants, etc.

Suitable active compounds are, for example, insect repellents, inorganic UV filters, such as, for example, $TiO_2$, UV A/BC protection filters (for example OMC, B3, MBC), including in encapsulated form, antiageing active compounds, vitamins and derivatives thereof (for example vitamin A, C, E, etc.), self-tanning agents (for example DHA, erythrulose, inter alia) and further cosmetic active compounds, such as, for example, bisabolol, LPO, VTA, ectoine, emblica, allantoin, bioflavonoids and derivatives thereof.

Organic UV filters are generally incorporated into cosmetic formulations in an amount of 0.5 to 10% by weight, preferably 1 to 8% by weight, and inorganic filters are incorporated in an amount of 0.1 to 30% by weight. The compositions according to the invention may, in addition, comprise further conventional skin-protecting or skin-care active compounds. These may in principle be all active compounds known to the person skilled in the art. Particularly preferred active compounds are pyrimidinecarboxylic acids and/or aryl oximes.

Of the cosmetic applications, particular mention may be made of the use of ectoine and ectoine derivatives for the care of aged, dry or irritated skin. Thus, European Patent Application EP-A-0 671 161 describes, in particular, that ectoine and hydroxyectoine are employed in cosmetic compositions, such as powders, soaps, surfactant-containing cleansing products, lipsticks, rouge, make-up, care creams and sunscreen preparations.

In self-tanning creams, lotions, sprays, etc., comprising, for example, the self-tanning agent DHA (dihydroxyacetone) and an effect pigment with a final $TiO_2$ layer, the DHA is slowly degraded in the formulation. On use of the glass flakes according to the invention instead of the $TiO_2$-coated effect pigments in the formulation, the action of the DHA is fully retained.

It goes without saying that, for the various applications, the glass flakes according to the invention may also advantageously be used as a mixture with effect pigments, such as, for example, pearlescent pigments, interference pigments, goniochromatic pigments, BiOCl flakes, multilayered pigments, metal pigments, organic dyes, organic colored pigments and other pigments, such as, for example, transparent and opaque white, colored and black pigments, and also with flake-form iron oxides, holographic pigments, LCPs (liquid crystal polymers) and conventional transparent, colored and black luster pigments based on metal-oxide-coated mica flakes and $SiO_2$ flakes, etc. The glass flakes according to the invention can be mixed with commercially available (effect) pigments in any ratio. The glass flake:pigment weight ratio can be 1:99 to 99:1, depending on the color intensity. In the case of colored textures, the pigment proportion is higher than in the case of less-colored textures.

Suitable colorants in cosmetics are, in particular, effect pigments, such as, for example, pearlescent pigments, including multilayered pigments or interference pigments. The pearlescent pigments used are pigments based on flake-form, transparent or semitransparent substrates comprising, for example, phyllosilicates, such as, for example, natural or synthetic mica, talc, sericite, kaolin or other silicate materials, which are coated with colored or colorless metal oxides, such as, for example, $TiO_2$, titanium suboxides, titanium oxynitrides, $Fe_2O_3$, $Fe_3O_4$, FeOOH, $SnO_2$, $Cr_2O_3$, ZnO, CuO, NiO and other metal oxides, alone or in a mixture, in a single layer or in successive layers.

Pearlescent pigments are known, for example, from the German patents and patent applications 14 67 468, 19 59 998, 20 09 566, 22 14 454, 22 15 191, 22 44 298, 23 13 331, 25 22 572, 31 37 808, 31 37 809, 31 51 343, 31 51 354, 31 51 355, 32 11 602, 32 35 017 and P 38 42 330 and are commercially available, for example under the trade names Iriodin®, Timiron®, Xirona®, Colorona®, Dichrona® from Merck KGaA, Darmstadt, Germany, and/or Rona, USA. Particularly preferred pigment preparations comprise $TiO_2$/mica, $Fe_2O_3$/mica and/or $TiO_2/Fe_2O_3$/mica pigments. The pearlescent pigments may additionally also have a layer of Berlin Blue or Carmine Red on the surface.

Preference is furthermore given to coated or uncoated BiOCl pigments, $TiO_2$- and/or $Fe_2O_3$-coated $SiO_2$, glass or $Al_2O_3$ flakes. The coating of the $SiO_2$ flakes with one or more metal oxides can be carried out, for example, as described in WO 93/08237 (wet-chemical coating) or DE-A 196 14 637 (CVD process).

The multilayered pigments known, for example, from German Laid-Open Specifications DE 196 18 563, DE 196 18 566, DE 196 18 569, DE 197 07 805, DE 197 07 806, DE 197 46 067 are based on a flake-form, transparent, colored or colorless matrix consisting of mica (synthetic or natural), $SiO_2$ flakes, glass flakes, $Al_2O_3$ flakes, polymer flakes, and generally have a thickness of between 0.3 and 5 μm, in particular between 0.4 and 2.0 μm. The size in the two other dimensions is usually between 1 and 250 μm, preferably between 2 and 100 μm, and in particular between 5 and 40 μm. The multilayered pigments consist of the matrix (substrate) coated with metal oxides (at least two). The coating of the substrate flakes mica, $SiO_2$ flakes, glass flakes, $Al_2O_3$ flakes with a plurality of layers is carried out in such a way that a layer structure, preferably consisting of alternating high- and low-refractive-index layers, is formed. The multilayered pigments preferably comprise 2, 3, 4, 5, 6 or 7 layers, in particular 3, 4 or 5 layers. Suitable high-refractive-index metal oxides are, for example, titanium dioxide, zirconium oxide, zinc oxide, iron oxides, iron/titanium oxides (iron titanates)

and/or chromium oxide, in particular $TiO_2$ and/or $Fe_2O_3$. The low-refractive-index oxides employed are $SiO_2$ and $Al_2O_3$. However, $MgF_2$ or an organic polymer (for example acrylate) can also be employed for this purpose. The coating of the substrate flakes can be carried out, for example, as described, in WO 93/08237 (wet-chemical coating) or DE-A 196 14 637 (CVD process). Coating means that the substrate is completely covered with one or more layers.

Particularly preferred multilayered pigments based on mica (natural or synthetic), glass flakes, $Al_2O_3$ flakes, $Fe_2O_3$ flakes, $SiO_2$ flakes comprise a $TiO_2$—$SiO_2$—$TiO_2$ layer sequence.

The interference pigments are preferably pigments based on natural and synthetic mica, glass flakes, $SiO_2$ flakes, $Al_2O_3$ flakes, which are coated with colored or colorless metal oxides, such as, for example, $TiO_2$, titanium suboxides, titanium oxynitrides, $Fe_2O_3$, $Fe_3O_4$, $SnO_2$, $Cr_2O_3$, ZnO, CuO, NiO and other metal oxides, alone or in a mixture, in a single layer or in successive layers.

Suitable flake-form colorants are, in particular, pearlescent pigments, in particular based on natural or synthetic mica, $SiO_2$ flakes, $Fe_2O_3$ flakes, glass flakes or $Al_2O_3$ flakes, which are covered only with a metal-oxide layer, metal-effect pigments (Al flakes, bronzes), optically variable pigments (OVPs), liquid-crystal polymer pigments (LCPs) or holographic pigments.

The spherical colorants include, in particular, $TiO_2$, colored $SiO_2$, $CaSO_4$, iron oxides, chromium oxides, carbon black, organic colored pigments, such as, for example, anthraquinone pigments, quinacridone pigments, diketopyrrolopyrrole pigments, phthalocyanine pigments, azo pigments, isoindoline pigments. The needle-shaped pigments are preferably BiOCl, colored glass fibres, α-FeOOH, organic colored pigments, such as, for example, azo pigments, β-phthalocyanine Cl Blue 15.3, Cromophtal Yellow 8GN (Ciba-Geigy), Irgalith Blue PD56 (Ciba-Geigy), azomethine/copper complex CI Yellow 129, Irgazine Yellow 5GT (Ciba-Geigy).

Suitable organic colored pigments and dyes are of natural or synthetic origin, such as, for example, chromium oxide and ultramarine.

The glass flakes, which are preferably used as fillers in cosmetic formulations, may of course also be mixed or employed with other known fillers. Fillers which may be mentioned are, for example, synthetic organic polymers, polymethyl methacrylate, methyl methacrylate crosspolymer, natural and synthetic mica, nylon powder, pure or filled melamine resins, talc, $SiO_2$, glass powder, glass beads, kaolin, oxides or hydroxides of aluminium, magnesium, calcium, zinc, BiOCl, barium sulfate, calcium sulfate, calcium carbonate, magnesium carbonate, basic alkaline-earth metal carbonates, such as, for example, calcium carbonate or magnesium carbonate, carbon, and physical or chemical combinations of these substances.

There are no restrictions regarding the particle shape of the other fillers. In accordance with requirements, they can be, for example, irregular, flake-form, spherical or needle-shaped.

Nanoscale dielectrics may also be incorporated in order to improve the skin feel. Examples of additions of this type are $Al_2O_3$, $SiO_2$, ZnO or $TiO_2$, which are usually added to the formulation in amounts of 0.01-15% by weight.

The formulations comprising the glass flakes according to the invention can belong to the lipophilic, hydrophilic or hydrophobic type. In the case of heterogeneous formulations having discrete aqueous and non-aqueous phases, the glass flakes according to the invention may be present in each case in only one of the two phases or alternatively distributed over both phases.

The pH values of the formulations can be between 1 and 14, preferably between 2 and 11 and particularly preferably between 5 and 8.

Application forms of the cosmetic formulations which may be mentioned are, for example, solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower preparations. Besides the glass flakes according to the invention, any desired customary carriers, assistants and, if desired, further active compounds may be added to the composition.

Ointments, pastes, creams and gels may comprise the customary carriers, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary carriers, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary carriers, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary carriers, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary carriers, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary carriers, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary carriers, such as synthetic oils, such as, for example, fatty acid esters, fatty alcohols, silicone oils, natural oils, such as vegetable oils and oily plant extracts, paraffin oils, lanolin oils, or mixtures of these substances.

The cosmetic compositions may exist in various forms. Thus, they can be, for example, a solution, a water-free composition, an emulsion or microemulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoines in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Further embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

Solid sticks consist of natural or synthetic waxes and oils, fatty alcohols, fatty acids, fatty acid esters, lanolin and other fatty substances.

Cosmetic oils are preferably mineral oil, hydrogenated polyisobutene, synthetic squalane or squalane prepared from natural products, cosmetic esters or ethers, which may be branched or unbranched, saturated or unsaturated, vegetable oils or mixtures thereof.

If a composition is formulated as an aerosol, the customary propellants, such as alkanes, fluoroalkanes and chlorofluoroalkanes, are generally used.

The cosmetic composition may also be used to protect the hair against photochemical damage in order to prevent color changes, bleaching or damage of a mechanical nature. In this case, a suitable formulation is in the form of a rinse-out shampoo, lotion, gel or emulsion, the composition in question being applied before or after shampooing, before or after coloring or bleaching or before or after permanent waving. It is also possible to select a composition in the form of a lotion or gel for styling or treating the hair, in the form of a lotion or gel for brushing or blow-waving, in the form of a hair lacquer, permanent waving composition, colorant or bleach for the hair. The composition having light-protection properties may comprise assistants, such as surfactants, thickeners, polymers, softeners, preservatives, foam stabilisers, electrolytes, organic solvents, silicone derivatives, oils, waxes, antigrease agents, dyes and/or pigments which color the composition itself or the hair, or other ingredients usually used for hair care.

The glass flakes according to the invention can be used as fillers, for example in lipsticks, lip gloss, rouge, eyeliner, eye shadow, (volume) mascara, nail varnishes, day creams, night creams, body lotions, cleansing milk, body powder, hair gels, hair masks, hair rinses, hair shampoos, shower gels, shower oils, bath oils, sunscreen, pre-sun and after-sun preparations, tanning lotions, tanning sprays, make-ups, lotions, soaps, bath salts, toothpastes, face masks, compact powders, loose powders and gels, etc. Products of this type are produced in a manner as is known to the person skilled in the art in this area.

The present invention furthermore relates to cosmetic formulations comprising the glass substrates according to the invention.

The invention thus also relates to the use of the glass flakes according to the invention as filler, in particular in care and decorative cosmetics, and in paints, coatings, automobile paints, powder coatings, printing inks, security printing inks, plastics, paper, in paper coatings, in pigment pastes with water, organic and/or aqueous solvents, for the preparation of pigment compositions and dry preparations, such as, for example, granules. The glass flakes according to the invention are preferably employed as functional filler since the glass flakes may improve the applicational properties, the skin feel, the pay-off and the compressibility of powders. Furthermore, they may reduce the fatty, sticky aspect of the formulation, increase the richness of emulsions, influence the viscosity properties and texture and improve the drying time of, for example, mascara, eyeliners, etc.

The following examples are intended to explain the invention in greater detail, but without restricting it. Above and below, all percentages are per cent by weight.

The oil absorption value is a conventional characteristic number for the characterisation of the oil requirement of pigments and is determined in accordance with DIN EN ISO 787-5: 1995-10.

EXAMPLES

The compositions of the glass flakes are shown in the following table:

| Composition | Example 1 | Example 2 | Example 3 | Example 4 | Example 5 | Example 6 |
|---|---|---|---|---|---|---|
| $SiO_2$ | 65-70 | 64-70 | 65 | 63.0-67.0 | 65-72 | 52-56 |
| $Al_2O_3$ | 2-6 | 3-6 | 4 | 3.0-5.0 | 1-7 | 12-16 |
| CaO | 4-9 | 3-7 | 14 | 4.0-7.0 | 4-11 | 16-25 |
| MgO | 0-5 | 1-4 | 3 | 2.0-4.0 | 0-5 | 0-6 |
| $B_2O_3$ | 2-7 | 2-5 | 5.5 | 4.0-7.0 | 0-8 | 5-13 |
| $Na_2O + K_2O$ | 9-13 | | 8.5 | | 9-13 | 0-0.8 |
| $Na_2O$ | | 8-13 | | 14.0-17.0 | | |
| $K_2O$ | | 0-3 | | 0-2.0 | | |
| ZnO | 1-6 | 1-5 | 0 | <0.1 | 0-6 | |
| $FeO/Fe_2O_3$ | | | 0 | <0.2 | | |
| $TiO_2$ | | 0-1 | | | | |
| ZnO | | | | <0.1 | | |
| BaO | | | | <0.1 | | |
| $F_2$ | | | | <1.0 | | |

Example 1

Production of Glass Flakes Having a Thickness of 900 nm from C Glass

A glass jet of molten C glass falls vertically onto a rotating cup. The glass jet hits the cup in such a way that the molten glass is transported upwards at the cup rim and spills over the cup rim. The glass is supported horizontally by centrifugal forces and enters a gap between two plates arranged in parallel. The parallel plates are located in a vacuum chamber, and consequently the glass lamella formed is held horizontally by the vacuum and thus does not touch the plates. On solidification of the glass, the planar C glass flakes form. The flakes are ground to a 15-150 μm fraction in a conventional air-jet mill. The glass flakes produced in this way have an oil absorption value of 75.

Example 2

Production of Glass Flakes Having a Thickness of 700 nm from ECR Glass

A glass jet of molten ECR glass falls vertically onto a rotating cup. The glass jet hits the cup in such a way that the molten glass is transported upwards at the cup rim and spills over the cup rim. The glass is supported horizontally by centrifugal forces and enters a gap between two plates arranged in parallel. The parallel plates are located in a vacuum chamber, and consequently the glass lamella formed is held horizontally by the vacuum and thus does not touch the plates. On solidification of the glass, the planar ECR glass flakes form. The flakes are ground to a 5-50 μm fraction in a conventional air-jet mill. The glass flakes produced in this way have an oil absorption value of 80.

Example 3

Production of Glass Flakes Having a Thickness of 800 nm from C Glass

A glass jet of molten C glass falls vertically onto a rotating cup. The glass jet hits the cup in such a way that the molten glass is transported upwards at the cup rim and spills over the cup rim. The glass is supported horizontally by centrifugal forces and enters a gap between two plates arranged in parallel. The parallel plates are located in a vacuum chamber, and consequently the glass lamella formed is held horizontally by the vacuum and thus does not touch the plates. On solidification of the glass, the planar C glass flakes form. The flakes are ground to a 10-100 μm fraction in a conventional air-jet mill. The glass flakes produced in this way have an oil absorption value of 75.

Example 4

Production of Glass Flakes Having a Thickness of 700 nm from C Glass

A glass jet of molten C glass falls vertically onto a rotating cup. The glass jet hits the cup in such a way that the molten glass is transported upwards at the cup rim and spills over the cup rim. The glass is supported horizontally by centrifugal forces and enters a gap between two plates arranged in parallel. The parallel plates are located in a vacuum chamber, and consequently the glass lamella formed is held horizontally by the vacuum and thus does not touch the plates. On solidification of the glass, the planar C glass flakes form. The flakes are ground to a 15-150 μm fraction in a conventional air-jet mill. The glass flakes produced in this way have an oil absorption value of 85.

Example 5

Production of Glass Flakes Having a Thickness of 750 nm from C Glass

A glass jet of molten C glass falls vertically onto a rotating cup. The glass jet hits the cup in such a way that the molten glass is transported upwards at the cup rim and spills over the cup rim. The glass is supported horizontally by centrifugal forces and enters a gap between two plates arranged in parallel. The parallel plates are located in a vacuum chamber, and consequently the glass lamella formed is held horizontally by the vacuum and thus does not touch the plates. On solidification of the glass, the planar C glass flakes form. The flakes are ground to a 10-100 μm fraction in a conventional air-jet mill. The glass flakes produced in this way have an oil absorption value of 65.

Example 6

Production of Glass Flakes Having a Thickness of 800 nm from E Glass

A glass jet of molten E glass falls vertically onto a rotating cup. The glass jet hits the cup in such a way that the molten glass is transported upwards at the cup rim and spills over the cup rim. The glass is supported horizontally by centrifugal forces and enters a gap between two plates arranged in parallel. The parallel plates are located in a vacuum chamber, and consequently the glass lamella formed is held horizontally by the vacuum and thus does not touch the plates. On solidification of the glass, the planar E glass flakes form. The flakes are ground to a 5-50 μm fraction in a conventional air-jet mill. The glass flakes produced in this way have an oil absorption value of 55.

USE EXAMPLES

Example A1

Cream Conditioner

| Phase | Raw material | INCI | % |
|---|---|---|---|
| A | Water | AQUA (WATER) | 75.20 |
|  | Glass flakes according to Example 2 (1) |  | 5.00 |
|  | Luviquat Hold | POLYQUATERNIUM-46 | 5.00 |
|  | Luviquat PQ 11 | POLYQUATERNIUM-11 | 2.00 |
|  | Butylene glycol | BUTYLENE GLYCOL | 3.00 |
| B | Cremophor A 6 | CETEARETH-6 AND STEARYL ALCOHOL | 3.00 |
|  | Ammonyx 4 | STEARALKONIUM CHLORIDE | 3.00 |
|  | Lanette Wax O | CETEARYL ALCOHOL | 2.00 |
|  | Eusolex 2292 | OCTYL METHOXYCINNAMATE | 0.10 |
| C | Vitamin E acetate | TOCOPHERYL ACETATE | 0.50 |
|  | Bisabolol | BISABOLOL | 0.10 |
|  | Perfume | PARFUM | 0.10 |
|  | Germaben II | PROPYLENE GLYCOL, DIAZOLIDINYL UREA, METHYLPARABEN PROPYLPARABEN | 1.00 |

Preparation:
Disperse the pigments in the water of phase A and add the remaining raw materials. After each addition, stir well and subsequently heat to 75° C. Mix the raw materials of phase B, heat to 75-80° C. and add to phase A. Mix until a homogeneous distribution is obtained. Add phase C at 45° C.

Example A2

Shower Gel

| Phase | Raw material | INCI | % |
|---|---|---|---|
| A | Ronastar ® Golden Sparks (1) | CALCIUM ALUMINUM BOROSILICATE, SILICA, CI 77891 TITANIUM DIOXIDE), TIN OXIDE | 0.05 |
|  | Glass flakes according to Example 1 (1) |  | 0.20 |
|  | Keltrol CG-SFT (2) | XANTHAN GUM | 1.10 |
|  | Water, demineralised | WATER, AQUA (WATER) | 54.80 |
| B | Plantacare 2000UP (3) | DECYL GLUCOSIDE | 20.00 |
|  | Texapon ASV 50 (3) | SODIUM LAURETH SULFATE, SODIUM LAURETH-8 SODIUM LAURETH SULFATE, SODIUM LAURETH-8 MAGNESIUM LAURETH-8 SULFATE, SODIUM OLETH SULFATE, MAGNESIUM OLETH SULFATE | 3.60 |

-continued

| Phase | Raw material | INCI | % |
|---|---|---|---|
| | Bronidox L (3) | PROPYLENE GLYCOL, 5-BROMO-5-NITRO-1,3-DIOXANE | 0.30 |
| | Frag 280851 Fruit Cocktail (4) | PARFUM | 0.20 |
| | 0.1% of Sicovit Quinoline Yellow 70 E 104 in water (5) | AQUA (WATER), WATER, CI 47005 (ACID YELLO ACID YELLOW 3W 3), | 8.30 |
| | 0.1% of Dragocolor True Blue in water (6) | AQUA (WATER), WATER, CI 42090 (FD&C BLUE NO. 1), FD&C BLUE NO. 1 | 1.30 |
| C | Citric acid monohydrate (1) | CITRIC ACID | 0.15 |
| | Water, demineralised | WATER, AQUA (WATER) | 10.00 |

Preparation:

Phase A: Introduce the water into the reactor and stir in the pigment. Slowly scatter in the Keltrol CG-SFT with stirring and stir until it has completely dissolved (do not homogenise). Add the constituents of phase B individually to phase A. Dissolve the citric acid monohydrate in water and add to the batch and stir slowly until everything is homogeneously distributed. Adjust the pH to 6.0-6.5 with addition of citric acid (if required).

Sources of Supply:
(1) Merck KGaA/Rona®
(2) C. P. Kelco
(3) Cognis GmbH
(4) Drom
(5) BASF AG
(6) Symrise Example A3

Eye Shadow

| Phase | Raw material | INCI | % |
|---|---|---|---|
| A | Xirona ® Magic Mauve (1) | SILICA, CI 77891 (TITANIUM DIOXIDE), TIN OXIDE | 27.00 |
| | Microna ® Matte Blue (1) | CI 77510 (FERRIC FERROCYANIDE), MICA | 3.00 |
| | Talc (1) | TALC | 34.50 |
| | Glass flakes according to Example 2 (1) | | 15.00 |
| | Potato starch (2) | POTATO STARCH, SOLANUM TUBEROSUM (POTATO STARCH) | 7.50 |
| | Magnesium stearate (1) | MAGNESIUM STEARATE | 2.50 |
| B | Isopropyl stearate (3) | ISOPROPYL STEARATE | 9.14 |
| | Cetyl palmitate (1) | CETYL PALMITATE | 0.53 |
| | Ewalin 1751 (4) | PETROLATUM | 0.53 |
| | Perfume oil Elegance + 79228 D MF (5) | PARFUM | 0.20 |
| | Propyl 4-hydroxybenzoate (1) | PROPYLPARABEN | 0.10 |

Preparation:

Combine and pre-mix the constituents of phase A. Subsequently add the molten phase B dropwise to the powder mixture with stirring. The powders are transferred into powder pans of large diameter and pressed at 80 bar.

Sources of Supply:
(1) Merck KGaA/Rona®
(2) Suedstaerke GmbH
(3) Cognis GmbH
(4) H. Erhard Wagner GmbH
(5) Symrise Example A4

Wrinkle-Reducing Day Cream

| Phase | Raw material | INCI | % |
|---|---|---|---|
| A | Ronasphere ® LDP(1) | SILICA, CI 77891 (TITANIUM DIOXIDE), CI 77491 (IRON OXIDES) | 5.00 |
| | Veegum HV (2) | MAGNESIUM ALUMINUM SILICATE | 1.00 |
| | Glass flakes according to Example 2 (1) | | 5.00 |
| | Karion F liquid (1) | SORBITOL | 3.00 |
| | Methyl 4-hydroxybenzoate (1) | METHYLPARABEN | 0.18 |
| | Water, demineralised | AQUA (WATER) | 51.44 |
| B | Arlacel 165 VP (3) | GLYCERYL STEARATE, PEG-100 STEARATE | 5.00 |
| | Lanette O (4) | CETEARYL ALCOHOL | 1.50 |
| | Miglyol 812 N (5) | CAPRYLIC/CAPRIC TRIGLYCERIDE | 7.00 |
| | Shea butter solid (6) | BUTYROSPERMUM PARKII (SHEA BUTTER) | 2.00 |
| | Cetiol SN (4) | CETEARYL ISONONANOATE | 7.00 |
| | Eutanol G (4) | OCTYLDODECANOL | 7.50 |
| | Emulgade PL 68/50 (4) | CETEARYL ALCOHOL, CETEARYL GLUCOSIDE | 2.00 |
| | Propyl 4-hydroxybenzoate (1) | PROPYLPARABEN | 0.08 |
| C | Perfume oil 200 530 (7) | PARFUM | 0.20 |
| | Dow Corning 345 (8) | CYCLOMETHICONE | 2.00 |
| | Euxyl K 400 (9) | PHENOXYETHANOL, METHYLDIBROMO GLUTARONITRILE | 0.10 |
| | Citric acid monohydrate (1) | CITRIC ACID | 0.00 |

Preparation:

Warm phase B until the solution is clear. Disperse the Veegum in the water of phase A, add the remaining raw materials, heat to 80° C. and add phase B. Homogenise phases A/B. Cool to 40° C. with stirring and add phase C. Cool to room temperature and adjust to pH 6.0.

Sources of Supply:
(1) Merck KGaA/Rona®
(2) Vanderbilt
(3) Uniqema
(4) Cognis GmbH
(5) Sasol Germany GmbH
(6) H. Erhard Wagner GmbH
(7) Fragrance Resources
(8) Dow Corning
(9) Schülke & Mayr GmbH

Example A5

Sparkling Body Cream

| Phase | Raw material | INCI | % |
|---|---|---|---|
| A | Ronastar ® Copper Sparks (1) | CALCIUM ALUMINUM BOROSILICATE, SILICA, CI 77891 (TITANIUM DIOXIDE), TIN OXIDE | 3.00 |
| | Glass flakes according to Example 5 (1) | | 3.00 |
| | Water, demineralised | WATER, AQUA (WATER) | 36.60 |
| | Carbopol Ultrez 21 (2) | ACRYLATES/C10-30 ALKYL ACRYLATE CROSSPOLYMER | 0.60 |
| | Citric acid monohydrate (1) | CROSSPOLYMER | 0.00 |
| B | Water, demineralised | WATER, AQUA (WATER) | 26.35 |
| | 1,2-Propanediol (1) | PROPYLENE GLYCOL | 3.00 |
| | RonaCare ® allantoin (1) | PROPYLENE GLYCOL | 0.20 |
| C | Liquid paraffin (1) | PARAFFINUM LIQUIDUM (MINERAL OIL), MINERAL OIL | 10.00 |
| | Cetiol V (3) | DECYL OLEATE | 6.00 |
| | Hostaphat KL 340 D (4) | TRILAURETH-4 PHOSPHATE | 3.00 |
| | Cetyl alcohol (1) | CETYL ALCOHOL | 2.00 |
| | Phenonip (5) | PHENOXYETHANOL, BUTYLPARABEN, ETHYLPARABEN, PROPYLPARABEN, METHYLPARABEN | 0.50 |
| D | Water, demineralised | WATER, AQUA (WATER) | 3.50 |
| | Triethanolamine | TRIETHANOLAMINE | 0.35 |
| E | Germall 115 (6) | IMIDAZOLIDINYL UREA | 0.30 |
| | Perfume oil Vogue (7) | PARFUM | 0.10 |
| | Water, demineralised | WATER, AQUA (WATER) | 1.50 |

Preparation:

Disperse the pearlescent pigment in the water of phase A. If necessary, acidify using a few drops of citric acid in order to reduce the viscosity. Scatter in the Carbopol with stirring. When completely dissolved, slowly stir in the predissolved phase B. Heat phases A/B and phase C to 80° C., stir phase C into phases A/B, homogenise, neutralise with phase D, homogenise again and cool with stirring. Dissolve the Germall 115 in the water of phase E at 40° C. and add with stirring. Then add the perfume oil and cool to room temperature with stirring.

Sources of Supply:
(1) Merck KGaA/Rona®
(2) Noveon
(3) Cognis GmbH
(4) Clariant GmbH
(5) Nipa Laboratorien GmbH
(6) ISP Global Technologies
(7) Drom

Example A6

Creamy Eye Shadow

| Phase | Raw material | INCI | % |
|---|---|---|---|
| A | Xirona ® Golden Sky (1) | SILICA, CI 77891 (TITANIUM DIOXIDE), TIN OXIDE | 14.00 |
| | Glass flakes according to Example 3 (1) | | 6.00 |
| | Unipure Green LC 789 CF (2) | CI 77289 (CHROMIUM HYDROXIDE GREEN) | 3.00 |
| B | Crodamol PMP (3) | PPG-2 MYRISTYL ETHER PROPIONATE | 41.58 |
| | Syncrowax HGLC (3) | C18-36 ACID TRIGLYCERIDE | 11.00 |
| | Syncrowax HRC (3) | TRIBEHENIN | 3.30 |
| | Miglyol 812 N (4) | CAPRYLIC/CAPRIC TRIGLYCERIDE | 15.40 |
| | Stearic acid (1) | STEARIC ACID | 3.30 |
| | Antaron V-216 (5) | PVP/HEXADECENE COPOLYMER | 2.20 |
| | Oxynex ® K liquid (1) | PVP/HEXADECENE COPOLYMER, ASCORBIC ACID, CITRIC ACID | 0.11 |
| | Propyl 4-hydroxybenzoate (1) | PROPYLPARABEN | 0.11 |

Preparation:
Heat phase B to about 80° C. until everything has melted and cool to 65° C. The pearlescent pigment and the ground chromium oxide of phase A are then added with stirring. The eye shadow is packaged at 65° C.

Sources of Supply:
(1) Merck KGaA/Rona®
(2) Les Colorants Wackherr
(3) Croda GmbH
(4) Sasol Germany GmbH
(5) ISP Global Technologies

Example A7

Hair Styling Gel

| Phase | Raw material | INCI | % |
|---|---|---|---|
| A | Ronastar ® Blue Sparks (1) | CALCIUM ALUMINUM BOROSILICATE, CI 77891 CALCIUM ALUMINUM BOROSILICATE, CI 77891 | 2.55 |
|  | Xirona ® Silver (1) | ALUMINA, CI 77891 (TITANIUM DIOXIDE), TIN OXIDE | 0.40 |
|  | Colorona ® Patina Silver (1) | MICA, CI 77499 (IRON OXIDES), CI 77891 (TITANIUM DIOXIDE) | 0.05 |
|  | Glass flakes according to Example 2 (1) |  | 3.00 |
|  | Carbopol Ultrez 21 (2) | ACRYLATES/C10-30 ALKYL ACRYLATE CROSSPOLYMER | 0.90 |
|  | Water, demineralised | WATER, AQUA (WATER) | 47.00 |
| B | Luviskol K 30 powder (3) | PVP | 2.00 |
|  | Germaben II (4) | PROPYLENE GLYCOL, DIAZOLIDINYL UREA, METHYLPARABEN, PROPYLPARABEN | 1.00 |
|  | Triethanolamine extra pure (1) | TRIETHANOLAMINE | 2.16 |
|  | Water, demineralised | WATER, AQUA (WATER) | 40.94 |

Preparation:
Disperse the pearlescent pigments in the water of phase A and scatter in the Carbopol with stirring. When completely dissolved, slowly stir in the predissolved phase B.

Sources of Supply:
(1) Merck KGaA/Rona®
(2) Noveon
(3) BASF AG
(4) ISP Global Technologies

Example A8

Shampoo

| Phase | Raw material | INCI | % |
|---|---|---|---|
| A | Glass flakes according to Example 4 (1) |  | 3.00 |
|  | Carbopol ETD 2020 (2) | ACRYLATES/C10-30 ALKYL ACRYLATE CROSSPOLYMER | 0.90 |
|  | Water, demineralised | AQUA (WATER) | 60.60 |
| B | Triethanolamine extra pure (1) | TRIETHANOLAMINE | 0.90 |
|  | Water, demineralised | AQUA (WATER) | 10.00 |
| C | Plantacare 2000 UP (3) | DECYL GLUCOSIDE | 20.00 |
|  | Texapon ASV 50 (3) | SODIUM LAURETH SULFATE, SODIUM LAURETH-8, SULFATE, MAGNESIUM LAURETH SULFATE, SULFATE, MAGNESIUM LAURETH SULFATE, SULFATE, MAGNESIUM OLETH SULFATE | 4.35 |
|  | Bronidox L (3) | PROPYLENE GLYCOL, 5-BROMO-5-NITRO-1,3-DIOXANE | 0.20 |
|  | Perfume oil 200 524 (4) | PARFUM | 0.05 |
|  | Dye solution (q.s.) |  | 0.00 |

Preparation:
For phase A, stir the filler into the water. Acidify using a few drops of citric acid (10%) in order to reduce the viscosity, and slowly scatter in the Carbopol with stirring. When completely dissolved, slowly add phase B. The constituents of phase C are then added successively. Adjust the pH to 6.0-6.5.

Sources of Supply:
(1) Merck KGaA/Rona®
(2) Noveon
(3) Cognis GmbH
(4) Fragrance Resources

Example A9

Shimmering Body Powder

| Phase | Raw material | INCI | % |
|---|---|---|---|
| A | Timiron ® Karat Gold MP-24 (1) | MICA, CI 77891 (TITANIUM DIOXIDE), CI 77491 (IRON OXIDES) | 10.00 |
| B | Microna ® Matte Red (1) | CI 77491 (IRON OXIDES), MICA | 1.00 |
|  | Microna ® Matte Yellow (1) | MICA, CI 77492 (IRON OXIDES) | 1.00 |

| Phase | Raw material | INCI | % |
|---|---|---|---|
| | Ronasphere ® LDP (1) | SILICA, CI 77891 (TITANIUM DIOXIDE), CI 77491 (IRON OXIDES) | 4.00 |
| | Talc (1) | TALC | 25.00 |
| | Glass flakes according to Example 6 (1) | | 15.00 |
| | White clay (1) | KAOLIN | 14.70 |
| | Mica M (1) | MICA | 15.00 |
| | Silk mica (1) | MICA | 9.50 |
| | Propyl 4-hydroxybenzoate (1) | PROPYLPARABEN | 0.30 |
| C | Cetiol SQ (2) | SQUALANE | 2.00 |
| | Miglyol 812 N (3) | CAPRYLIC/CAPRIC TRIGLYCERIDE | 2.00 |
| | RonaCare ® tocopherol acetate (1) | TOCOPHERYL ACETATE | 0.20 |
| | Fragrance Baby Cotton DC10122/1 (4) | PARFUM | 0.30 |

Preparation:
Weigh out all constituents of phase B together and grind homogeneously in a mixer. Subsequently add phase C and continue mixing, then add phase A and grind briefly until the pearlescent pigment is uniformly distributed.
Sources of Supply:
(1) Merck KGaA/Rona®
(2) Cognis GmbH
(3) Sasol Germany GmbH
(4) Symrise

Example A10

Long-Lasting Lip Gloss

| Phase | Raw material | INCI | % |
|---|---|---|---|
| A | Xirona ® Le Rouge (1) | SILICA, CI 77491 (IRON OXIDES), | 7.70 |
| | Glass flakes according to Example 2 (1) | | 3.00 |
| | Ronastar ® Red Sparks (1) | CALCIUM ALUMINUM BOROSILICATE, CI 77891 CALCIUM ALUMINUM BOROSILICATE, CI 77891 | 3.30 |
| B | Indopol H 100 (2) | POLYBUTENE | 29.00 |
| | Jojoba Glaze LV (3) | *SIMMONDSIA CHINENSIS* (JOJOBA), JOJOBA, SEED OIL, ETHYLENE/ PROPYLENE/STYRENE COPOLYMER, BUTYLENE/ ETHYLENE/STYRENE COPOLYMER | 19.00 |
| | Jojoba Glaze HV (3) | *SIMMONDSIA CHINENSIS* (JOJOBA), JOJOBA, SEED OIL, ETHYLENE/ PROPYLENE/STYRENE COPOLYMER, BUTYLENE/ ETHYLENE/STYRENE COPOLYMER | 10.00 |
| | Castor oil (4) | CASTOR OIL, *RICINUS COMMUNIS* (CASTOR OIL) | 20.15 |
| | Beeswax, bleached (1) | BEESWAX, *CERA ALBA* (BEESWAX) | 4.00 |
| | Propyl 4-hydroxybenzoate (1) | PROPYLPARABEN | 0.10 |
| | Oxynex ® K liquid (1) | PEG-8, TOCOPHEROL, ASCORBYL PALMITATE, ASCORBIC ACID, CITRIC ACID | 0.05 |
| | Rubis Covapate W 4765 (5) | *RICINUS COMMUNIS* (CASTOR OIL), CASTOR OIL, CI 15850 (D&C RED NO. 7 CALCIUM LAKE), D&C RED NO. 7 CALCIUM LAKE | 2.00 |
| C | Neosil CT11 (6) | SILICA | 1.50 |
| | Fragrance Tendresse 75418C (7) | PARFUM | 0.20 |

Preparation:
Weigh out all constituents of phase B together, heat to 80° C. and stir well. Stir in the pigments of phase A, scatter in the Neosil with stirring and finally add the perfume. Transfer the homogeneous mixture into containers.
Sources of Supply:
(1) Merck KGaA/Rona®
(2) BP Lavera Sud
(3) Desert Whale
(4) Henry Lamotte GmbH
(5) Les Colorants Wackherr
(6) Ineos Silicas Limited
(7) Symrise

Example A11

Nail Varnish

| Phase | Raw material | INCI | % |
|---|---|---|---|
| A | Xirona ® Le Rouge (1) | SILICA, CI 77491 (IRON OXIDES), | 1.75 |
| | Glass flakes according to Example 2 (1) | | 1.00 |
| | Ronastar ® Red Sparks (1) | CALCIUM ALUMINUM BOROSILICATE, CI 77891 CALCIUM ALUMINUM BOROSILICATE, CI 77891 | 0.25 |
| | Colouring base ref. 690 (2) | BUTYL ACETATE, ETHYL ACETATE, NITROCELLULOSE, PHTHALIC, ANHYDRIDE/ TRIMELLITIC ANHYDRIDE/ GLYCOLS COPOLYMER, CI 15850 (D&C RED NO. 7 CALCIUM LAKE), D&C RED NO. 7 CALCIUM LAKE, ISOPROPYL ALCOHOL, ACETYL TRIBUTYL CITRATE, STEARALKONIUM HECTORITE | 2.00 |
| | Thixotropic nail varnish base 155 (2) | BUTYL ACETATE, ETHYL ACETATE, NITROCELLULOSE, ACETYL TRIBUTYL CITRATE, PHTHALIC ANHYDRIDE/ TRIMELLITIC ANHYDRIDE/ GLYCOLS COPOLYMER, ISOPROPYL ALCOHOL, STEARALKONIUM HECTORITE, ADIPIC ACID/FUMARIC ACID/PHTHALIC ACID/TRICYCLODECANE DIMETHANOL COPOLYMER, CITRIC ACID | 95.00 |

Preparation:
The pigments are weighed out together with the varnish base, mixed well by hand using a spatula and subsequently stirred at 1000 rpm for 10 min.
Sources of Supply:
(1) Merck KGaA/Rona®
(2) Durlin/Bergerac NC

Example A12

Volume Mascara

| Phase | Raw material | INCI | % |
|---|---|---|---|
| A | Ronastar ® Silver (1) | CALCIUM ALUMINUM BOROSILICATE, SILICA, CI 77891 (TITANIUM DIOXIDE), TIN OXIDE | 4.00 |
| | Timiron ® Splendid Blue (1) | CI 77891 (TITANIUM DIOXIDE), MICA, SILICA | 3.00 |
| | Mica Black (1) | CI 77499 (IRON OXIDES), MICA, CI 77891 (TITANIUM DIOXIDE) | 4.50 |
| | Glass flakes according to Example 5 (1) | | 4.00 |
| | Satin mica (1) | MICA | 2.00 |
| B | Dermacryl 79 (2) | ACRYLATES/OCTYLACRYLAMIDE COPOLYMER | 3.50 |
| | Beeswax, bleached (1) | BEESWAX, *CERA ALBA* (BEESWAX) | 3.00 |
| | Syncrowax HRC (3) | TRIBEHENIN | 3.50 |
| | Stearic acid (1) | STEARIC ACID | 5.00 |
| | Tegin M (4) | GLYCERYL STEARATE | 3.50 |
| | Tegosoft CT (4) | CAPRYLIC/CAPRIC TRIGLYCERIDE | 2.50 |
| | Dow Corning 556 (5) | PHENYL TRIMETHICONE | 2.00 |
| | RonaCare ® tocopherol acetate (1) | PHENYL TRIMETHICONE | 0.50 |
| | Phenonip (6) | PHENOXYETHANOL, BUTYLPARABEN, ETHYLPARABEN, PROPYLPARABEN, METHYLPARABEN | 0.80 |
| C | Water, demineralised | WATER, AQUA (WATER) | 53.65 |
| | AMP Ultra PC 1000 (7) | AMINOMETHYL PROPANOL | 1.25 |
| | 1,3-Butane diol (1) | BUTYLENE GLYCOL | 1.00 |
| | RonaCare ® Biotin Plus (1) | UREA, DISODIUM PHOSPHATE, BIOTIN, CITRIC ACID | 0.50 |
| D | Germall 115 (8) | IMIDAZOLIDINYL UREA | 0.30 |
| | Water, demineralised | WATER, AQUA (WATER) | 1.50 |

Preparation:

Melt all constituents of phase B apart from the Dermacryl 79 together at about 85° C., add the Dermacryl 79 with stirring and leave to stir for 20 min until everything is homogeneously distributed. Heat the constituents of phase C to about 85° C. Stir the pearlescent pigments of phase A into phase C. Add phase C to phase B, continue stirring and homogenise at 8000 rpm for 1 min using the Ultra-Turrax T25. Allow to cool with stirring and add phase D at 40° C.

Sources of Supply:
(1) Merck KGaA/Rona®
(2) National Starch & Chemical
(3) Croda GmbH
(4) Degussa-Goldschmidt AG
(5) Dow Corning
(6) Nipa Laboratorien GmbH
(7) Angus Chemie GmbH
(8) ISP Global Technologies

Example A13

Shimmering Foundation

| Phase | Raw material | INCI | % |
|---|---|---|---|
| A | Extender W (1) | MICA, CI 77891 (TITANIUM DIOXIDE) | 9.00 |
| | Microna ® Matte Yellow (1) | MICA, CI 77492 (IRON OXIDES) | 4.00 |
| | Microna ® Matte Red (1) | CI 77491 (IRON OXIDES), MICA | 0.40 |
| | Microna ® Matte Black (1) | CI 77499 (IRON OXIDES), MICA | 0.30 |
| | Timiron ® Supersheen MP-1001 (1) | MICA, CI 77891 (TITANIUM DIOXIDE) | 4.50 |
| | Glass flakes according to Example 2 (1) | | 8.00 |
| B | Blanose 7 HF (2) | CELLULOSE GUM | 0.20 |
| | Veegum (3) | MAGNESIUM ALUMINUM SILICATE | 1.00 |
| | Texapon K 1296 (4) | SODIUM LAURYL SULFATE | 0.60 |
| | Triethanolamine extra pure (1) | TRIETHANOLAMINE | 0.50 |
| | Titriplex ® III (1) | DISODIUM EDTA | 0.25 |
| | Methyl 4-hydroxybenzoate (1) | METHYLPARABEN | 0.15 |
| | 1,2-Propanediol (1) | METHYLPARABEN | 10.90 |
| | Water, demineralised | AQUA (WATER) | 39.95 |

| Phase | Raw material | INCI | % |
|---|---|---|---|
| C | Isopropyl myristate (4) | ISOPROPYL MYRISTATE | 8.00 |
|   | Liquid paraffin (1) | PARAFFINUM LIQUIDUM (MINERAL OIL) | 3.60 |
|   | Crodamol SS (5) | PARAFFINUM LIQUIDUM (MINERAL OIL) | 2.60 |
|   | Monomuls 60-35 C (4) | HYDROGENATED PALM GLYCERIDES | 1.70 |
|   | Stearic acid (1) | STEARIC ACID | 1.50 |
|   | Eusolex ® 6300 (1) | 4-METHYLBENZYLIDENE CAMPHOR | 1.30 |
|   | Eusolex ® 4360 (1) | BENZOPHENONE-3 | 0.50 |
|   | RonaCare ® tocopherol acetate (1) | TOCOPHERYL ACETATE | 0.50 |
|   | Magnesium stearate (1) | MAGNESIUM STEARATE | 0.10 |
|   | Propyl 4-hydroxybenzoate (1) | PROPYLPARABEN | 0.05 |
| D | Perfume oil 200 529 (6) | PARFUM | 0.20 |
|   | Euxyl K 400 (7) | PHENOXYETHANOL, METHYL-DIBROMO GLUTARONITRILE | 0.20 |

Preparation:

Melt all constituents of phase C at about 75° C. and stir until everything has melted. Initially introduce the cold water of phase B, homogenise in the Blanose using the Turrax, scatter in the Veegum, and re-homogenise. Warm to 75° C. and dissolve the other constituents therein with stirring. Stir in the constituents of phase A. Add phase C at 75° C. with stirring and homogenise for 2 min. Cool the composition to 40° C. with stirring and add phase D. Cool further to room temperature with stirring and adjust to pH 6.0-6.5 (for example using citric acid solution).

Sources of Supply:
(1) Merck KGaA/Rona®
(2) Aqualon GmbH
(3) Vanderbilt
(4) Cognis GmbH
(5) Croda GmbH
(6) Fragrance Resources
(7) Schülke & Mayr GmbH Example A14

Tinted Day Cream with UV Protection

| Phase | Raw material | INCI | % |
|---|---|---|---|
| A | Eusolex ® 2292 (1) | ETHYLHEXYL METHOXYCINNAMATE, BHT | 3.00 |
|   | Eusolex ® 4360 (1) | BENZOPHENONE-3 | 3.00 |
|   | Arlacel 165 VP (2) | GLYCERYL STEARATE, PEG-100 STEARATE | 5.00 |
|   | Eusolex ® HMS (1) | HOMOSALATE | 5.00 |
|   | Arlacel 165 VP (2) | GLYCERYL STEARATE, PEG-100 STEARATE | 3.00 |
|   | Montanov 68 (3) | CETEARYL ALCOHOL, CETEARYL GLUCOSIDE | 3.00 |
|   | Dow Corning 345 (4) | CYCLOMETHICONE | 0.50 |
|   | Eutanol G (5) | OCTYLDODECANOL | 2.00 |
|   | Propyl 4-hydroxybenzoate (1) | PROPYLPARABEN | 0.05 |
| B | Eusolex ® T-2000 (1) | TITANIUM DIOXIDE, ALUMINA, SIMETHICONE | 3.00 |
|   | Extender W (1) | MICA, CI 77891 (TITANIUM DIOXIDE) | 4.00 |
|   | Microna ® Matte Yellow (1) | MICA, CI 77492 (IRON OXIDES) | 2.00 |
|   | Microna ® Matte Orange (1) | MICA, CI 77491 (IRON OXIDES) | 0.20 |
|   | Microna ® Matte Red (1) | CI 77491 (IRON OXIDES), MICA | 0.20 |
|   | Microna ® Matte Black (1) | CI 77499 (IRON OXIDES), MICA | 0.20 |
|   | Glass flakes according to Example 2 (1) |  | 3.00 |
|   | Karion FP, liquid (1) | SORBITOL | 5.00 |
|   | RonaCare ® allantoin (1) | ALLANTOIN | 0.50 |
|   | Keltrol T (6) | XANTHAN GUM | 0.20 |
|   | Chemag 2000 (deleted) (7) | XANTHAN GUM | 0.30 |
|   | Euxyl K 400 (8) | PHENOXYETHANOL, METHYLDI-BROMO GLUTARONITRILE | 0.10 |
|   | Methyl 4-hydroxybenzoate (1) | METHYLPARABEN | 0.15 |
|   | Water, demineralised | AQUA (WATER) | 56.60 |

Preparation:

Disperse all constituents apart from the Keltrol T in the water of phase B. Scatter the Keltrol into phase B with stirring and heat to 80° C. after 15 minutes. Heat phase A to 75° C. Slowly stir phase B into phase A and homogenise. Cool with stirring.

Sources of Supply:
(1) Merck KGaA/Rona®
(2) Uniqema
(3) Seppic
(4) Dow Corning
(5) Cognis GmbH
(6) C. P. Kelco
(7) Chemag AG
(8) Schülke & Mayr GmbH Example A15

Self-Tanning Care Cream (O/W)

| Phase | Raw material | INCI | [%] |
|---|---|---|---|
| A | | | |
| | Montanov 68 (1) | CETEARYL ALCOHOL, CETEARYL GLUCOSIDE | 4.00 |
| | Span 60 (2) | SORBITAN STEARATE | 1.50 |
| | Lanette O (3) | CETEARYL ALCOHOL | 1.00 |
| | Cosmacol ELI (4) | C12-13 ALKYL LACTATE | 3.00 |
| | Cosmacol EMI (4) | DI-C12-13 ALKYL MALATE | 1.50 |
| | Arlamol HD (2) | ISOHEXADECANE | 3.00 |
| | Dow Corning 9040 silicone elastomer blend (5) | CYCLOMETHICONE, DIMETHICONE CROSSPOLYMER | 1.00 |
| | RonaCare ® tocopherol acetate (6) | TOCOPHERYL ACETATE | 0.50 |
| | Propyl 4-hydroxybenzoate (6) | PROPYLPARABEN | 0.05 |
| B | | | |
| | RonaCare ® ectoine (6) | ECTOIN | 0.50 |
| | Glass flakes according to Example 2 (1) | | 2.00 |
| | Ronastar ® Silver (1) | CALCIUM ALUMINUM BOROSILICATE, SILICA, CI 77891 (TITANIUM DIOXIDE), TIN OXIDE | 2.00 |
| | Glycerol, anhydrous (6) | GLYCERIN | 2.00 |
| | FD&C Yellow No. 6 W082 (8) | CI 15985 | 0.01 |
| | Methyl 4-hydroxybenzoate (6) | METHYLPARABEN | 0.15 |
| | Water, demineralised | AQUA (WATER) | 62.09 |
| C | | | |
| | Sepigel 305 (1) | LAURETH-7, POLYACRYLAMIDE, C13-14 ISOPARAFFIN | 0.50 |
| D | | | |
| | Dihydroxyacetone (6) | DIHYDROXYACETONE | 5.00 |
| | Water, demineralised | AQUA (WATER) | 10.00 |
| E | | | |
| | Fragrance Babylon (9) | Parfum | 0.20 |

Preparation:

Phases A and B are warmed separately to 75° C. Phase B is then admixed slowly with phase A with stirring. Phase C is admixed with phases A/B using a hand stirrer at 60° C., and the mixture is homogenised. Allow to cool to 40° C. and stir in phase D and phase E.

Sources of Supply:
(1) Seppic
(2) Uniqema
(3) Cognis GmbH
(4) Condea Chimica D.A.C. S.p.A.
(5) Dow Corning
(6) Merck KGaA/Rona®
(7) D. D. Williamson
(8) Les Colorants Wackherr SA
(9) Drom The cosmetic formulations of Examples A1 to A15 are distinguished by very good skin tolerance, a good skin feel and good applicational properties.

The preceding examples can be repeated with similar success by substituting the generically or specifically described reactants and/or operating conditions of this invention for those used in the preceding examples.

The entire disclosures of all applications, patents and publications, cited herein and of corresponding German application No. 10 2006 014 095.8, filed Mar. 24, 2006, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A cosmetic formulation, comprising a glass filler having a matting effect which consists of uncoated glass flakes made of C or ECR glass having a thickness of 150-800 nm and a particle size of 3-35 μm, and an additional cosmetically suitable ingredient, which is not water.

2. The cosmetic formulation of claim 1 wherein the glass flakes have been mass-coloured with an inorganic colorant.

3. The cosmetic formulation of claim 2 wherein the colorant is a cation or complex anion of the elements Cu, Cr, Mn, Fe and Co and/or a combination thereof, or $TiO_2$ or an elemental noble metal.

4. The cosmetic formulation of claim 1 wherein the glass flakes have an aspect ratio of 5 to 200.

5. The cosmetic formulation of claim 1 wherein the glass flakes are amorphous.

6. The cosmetic formulation of claim 1 wherein the glass flakes are ECR glass.

7. The cosmetic formulation of claim 1 which is a care or decorative cosmetic formulation.

8. The cosmetic formulation of claim 1 which is a lipophilic, hydrophilic or hydrophobic formulation.

9. The cosmetic formulation of claim 1 wherein glass flakes are present according to claim 1 in an amount of 0.01-95% by weight, based on the formulation as a whole.

10. The cosmetic formulation of claim 1 further comprising one or more of water, polyol, polar or nonpolar oil, fat, wax, film former, polymer, copolymer, surfactant, free-radical scavenger, antioxidant, stabiliser, odor enhancer, silicone oil, emulsifier, solvent, preservative, thickener, rheological additive, fragrance, colorant, effect pigments, UV absorber, surface-active assistant and/or cosmetically active compounds.

11. The cosmetic formulation of claim 1 further comprising one or more fillers which are synthetic organic polymers, polymethyl methacrylate, methyl methacrylate cross-polymer, natural and/or synthetic mica, nylon powder, pure or filled melamine resins, talc, $SiO_2$, glass powder, glass beads, kaolin, oxides or hydroxides of aluminium, magnesium, calcium, zinc, BiOCl, barium sulfate, calcium sulfate, calcium carbonate, magnesium carbonate, basic alkaline-earth metal carbonates and/or carbon.

12. The cosmetic formulation of claim 1 wherein the glass flakes have a thickness of 200-600 nm.

13. The cosmetic formulation of claim 1 wherein the glass flakes have a refractive index of 1.2-2.1.

14. The cosmetic formulation of claim 1 wherein the glass flakes have a transparency of ≥95%.

15. The cosmetic formulation of claim 1, wherein the glass flakes are C glass.

16. The cosmetic formulation of claim 1, wherein the glass flakes have an oil absorption value (determined in accordance with DIN ISO 787-5: 1995-10) of 30 to 110.

17. The cosmetic formulation of claim 1, wherein the glass flakes have an oil absorption value (determined in accordance with DIN ISO 787-5: 1995-10) of 50 to 90.

18. The cosmetic formulation of claim 1, wherein the glass flakes have an oil absorption value (determined in accordance with DIN ISO 787-5: 1995-10) of 20 to 130.

19. The cosmetic formulation of claim 1, wherein the glass flakes contain $Na_2O$ at 8-13% and $K_2O$ at 0-3% by weight.

20. The cosmetic formulation of claim 1, wherein the glass flakes contain $Na_2O$ at 14-17% and $K_2O$ at 0-2% by weight.

* * * * *